United States Patent [19]

Hillion et al.

[11] Patent Number: 5,476,956
[45] Date of Patent: Dec. 19, 1995

[54] PROCESS FOR CODIMERIZATION OF DIENES AND OLEFINS

[75] Inventors: Gerard Hillion, Herblay; Robert Stern; Abakar Kotoko, both of Paris; Yves Chauvin, Le Pecq, all of France

[73] Assignee: Institut Francais Du Petrole, Rueil Malmaison, France

[21] Appl. No.: 232,984

[22] Filed: Apr. 25, 1994

[30] Foreign Application Priority Data

Apr. 23, 1993 [FR] France .................. 93 04922

[51] Int. Cl.⁶ .......................... C09F 7/06
[52] U.S. Cl. ............ 554/26; 554/124; 554/25; 554/162; 585/502; 585/506; 585/507
[58] Field of Search .............. 584/162, 26, 25, 584/124; 585/502, 506, 507

[56] References Cited

U.S. PATENT DOCUMENTS

| 3,502,738 | 3/1970 | Cramer | 260/680 |
| 3,636,122 | 1/1972 | Cramer et al. | 260/680 B |
| 3,640,898 | 2/1972 | Su | 252/429 |

FOREIGN PATENT DOCUMENTS 0475386  3/1992  European Pat. Off. .
4002008  7/1991  Germany .
WO91/11428  8/1991  WIPO .

OTHER PUBLICATIONS

Chemical Abstracts, vol. 66, #4, 11588.

*Primary Examiner*—José G. Dees
*Assistant Examiner*—Deborad D. Carr
*Attorney, Agent, or Firm*—Millen, White, Zelano, & Branigan

[57] ABSTRACT

Codimerization is conducted of at least one monoolefin, for example a monoolefinic hydrocarbon such as ethylene, propylene or 1-butene, a halogenated monoolefin such as vinyl chloride, or an olefinic functional compound such as methyl acrylate, acrylonitrile, allyl acetate or vinyl acetate, with at least one polyolefin containing at least two conjugated or unconjugated ethylene bonds, for example a diene hydrocarbon such as 1,3-butadiene, piperylene, or isoprene or a polyolefin containing a carboxylic function, such as a fatty acid or a fatty acid ester having 14 to 24 carbon atoms in the fatty chain derived, for example, from a natural oil. The reaction is carried out in the presence of a catalytic system having general formula $[RhX_4][YR_4]$ where X represents a halogen ion or a $SO_4^-$, $SO_3^-$, $OH^-$, $OR^-$ or $R^-$ group, at least one X being a halogen ion, Y represents a nitrogen atom or a phosphorous atom, and R represents an alkyl, cycloalkyl, alkenyl, aryl, alkylaryl, polystyryl, alkyl polystyryl or acyl radical.

18 Claims, No Drawings

PROCESS FOR CODIMERIZATION OF DIENES AND OLEFINS

The invention concerns a process for the production of co-dimers by addition of an olefin to various dienes, in particular fatty dienes.

BACKGROUND OF THE INVENTION

Olefins are known to react with butadiene or other dienes in the presence of rhodium complexes. These reactions are described, for example, in the following prior art documents: U.S. Pat. Nos. 3,013,066 and 3,636,122, which describe the use of a rhodium (I) complex with a cyclopentadiene ligand.

U.S. Pat. No. 3,640,898 describes the use of rhodium complexes comprising a rhodium salt or dimer and an amide or oxide of a phosphine amide.

U.S. Pat. No. 3,502,738 describes the use of dimeric rhodium complexes wherein the counter-ion is an alkali salt, a hydrogen atom $H^+$ or a nonsubstituted ammonium ion $NH_4^+$. Also, international patent application WO-A-91/11428 describes the use of a series of rhodium complexes or rhodium salts in the addition of ethylene to linoleic esters or linoleic esters containing conjugated ethylene bonds.

When the diene employed possesses poorly accessible double bonds, the reaction is very slow, as evidenced by the 24 hour period required to effect reaction between ethylene and linoleic esters in patent document WO-A- 91/11428. It therefore appears that the economic addition of ethylene to a fatty diene derivative poses difficulties.

SUMMARY OF THE INVENTION

The invention provides a process which accelerates addition of an olefin to fatty dienes, particularly conjugated dienes, by use of a very specific rhodium catalyst system.

In general terms, the process of the invention comprises the reaction of a monoolefin with a diolefin (or diene) in the presence of a catalytic system comprising a rhodium compound and a quaternary salt, the system being represented by the general formula

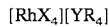

where X represents a halogen ion or a $SO_4^{--}$, $SO_3^-$, $OH^-$, $OR^-$ or $R^-$ group, at least one X being a halogen ion, Y represents a nitrogen atom or a phosphorous atom, and R, being the same or different, represents an alkyl, cycloalkyl, alkenyl, aryl, alkylaryl, polystyryl or acyl radical.

The monoolefin employed in the reaction may consist of any reactive monoolefin selected from ordinary monoolefins, (monoolefinic hydrocarbon), such as ethylene, propylene or 1-butene, halogenated monoolefins such as vinyl chloridle, and monoolefins containing different functional groups, in particular carboxylic or nitrile groups, such as alkyl acrylates, in particular methyl acrylate, acrylonitrile, allyl acetate or vinyl acetate.

The "diene" employed In the reaction on which the process of the invention is based is in general a compound containing at least two ethylene bonds, the bonds being conjugated or conjugatable in pairs. It may consist of an ordinary conjugated diene (a hydrocarbon diene) such as 1,3-butadiene, piperylene or isoprene, or at least one diene, triene or polyene containing a carboxylic function such as fatty acids having, for example, 14 to 26, preferably 18 to 24 carbon atoms, or their esters, in particular those derived from or contained in natural oils of plant or animal origin (sunflower, safflower, fish, linseed oils etc or, at a lower concentration, in polyunsaturated oils such as rape seed, peanut, walnut oil, etc).

It may also consist of a cyclic diene (for example cyclopentadiene, cyclohexadiene, cyclooctadiene, cyclododecatriene or norbornadiene, or dicyclopentadiene).

The fatty acids (dienes, trienes or tetraenes) may be conjugated or conjugatable and used as they are or as their esters with alcohols containing 1 to 18 carbon atoms, for example monofunctional alcohols (such as methanol or ethanol), difunctional alcohols (such as neopentylglycol) or trifunctional alcohols (such as propane trimethylol or glycerol).

Within the context of the invention, the term "conjugatable polyolefins" means compounds containing at least two ethylenic double bonds separated by 1 or 2 carbon atoms.

The rhodium compound used in the catalytic system is preferably hydrated rhodium chloride, and the quaternary salt is of the type:

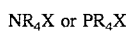

where R and X are as defined above; R is preferably a methyl, ethyl, propyl, butyl, pentyl, hexyl, octyl, decyl, dodecyl, hexadecyl, octadecyl, benzyl, polystyryl or methylpolystyryl radical; X preferably represents a halide or sulphate ($SO_4^{--}$) anion, or the sulphonate anion ($SO_3^-$) of a resin, or a hydroxyl anion ($OH^-$).

The catalyst is generally used in a solvent selected, for example, from chloroform, dichloroethane, alcohols (such as methanol or ethanol), saturated hydrocarbons (such as heptane or dodecane), or aromatics or alkylaromatics (such as benzene, toluene or a xylene) and mixtures thereof.

The reaction is carried out at a pressure of, for example, 0.1 to 30 MPa, preferably 0.4 to 3 MPa, and a temperature of 20° C. to 160° C., preferably 80° C. to 120° C.

The products obtained from the process of the invention are co-dimers or mixtures of co-dimers with 1 or 2 branches on the "diene" chain, possibly 3 branches if, for example, a compound containing three ethylene bonds is used, such as linoleic acid or an ester thereof.

The products of the invention where the initial polyolefins are carboxylic compounds, such as fatty acids or esters thereof, have particular application in the preparation of lubricants and emulsifying agents.

The following examples illustrate the invention:

EXAMPLE 1

The effects of different quaternary salts in the presence of trihydrated rhodium chloride were tested in this example.

The advantage of using quaternary salts was made clear. It could be seen that the 1:1 product (one ethylene for one ester) had excellent selectivity and increased rate compared with a system without the quaternary salt. There were, however, differences between the quaternary salts.

The catalytic solution in each test was constituted by 0.37 mmol of $RhCl_3.3H_2O$ and 0.37 mmol of the quaternary salt in 15 ml of chloroform.

176.8 mmol of the methyl ester of 54% conjugated sunflower seed oil was introduced into 50 ml of heptane at a pressure of 2 MPa and a temperature of 100° C. The reaction was carried out at constant pressure.

The molar ratio the ester and rhodium chloride was of the order of 480, except for test 10, conducted in heptane, where the molar ration was 780.

TABLE 1

| No | Quaternary salt | Time hours | Prd 1:1 weight % | Prd 2:1 weight % |
|----|-----------------|------------|------------------|------------------|
| 1  | TeMB A          | 2          | 4.5              | 0                |
| 2  | TriMSB A        | 2          | 20               | 0                |
| 3  | TePB A          | 2          | 29.3             | 0                |
| 4  | TeBuB A         | 2.75       | 70               | 0                |
| 5  | TeHB A          | 2          | 81.6             | 0                |
| 6  | TeHi A          | 2          | 2                | 0                |
| 7  | TeOF A          | 5          | 40.5             | 0                |
| 8  | BDSCl           | 2.3        | 74.4             | 8                |
| 9  | TeBuCl          | 2          | 71               | 2                |
| 10 | TePhBrP         | 0.6        | 1                | 0                |
| 11 | 0               | 2.5        | 2.5              | 0                |

Prd 1:1: 1-ethylene/1 fatty ester,

Prd 2:1: 2 ethylene/1 fatty ester,

TeMB A: Tetramethyl ammonium bromide,

TriMSB A: Trimethylstearyl ammonium bromide,

TePB A: Tetrapropyl ammonium bromide,

TeBuB A: Tetrabutyl ammonium bromide,

A TeHB: Tetrahexyl ammonium bromide,

TeHi A: Tetrahexyl ammonium iodide,

TeOF A: Tetraoctyl ammonium fluoride,

BDSCl: Benzyldimethylstearyl ammonium chloride, monohydrated,

TeBuClP: Tetrabutyl phosphonium chloride,

TePhBrP: Tetraphenyl phosphonium bromide.

The most hydrophobic compounds were in general the most active.

Three characteristics of the quaternary salt had an effect on the reactivity of the rhodium chloride. These were the length of the alkyl group, the nature of the halogen and the nature of the atom at the centre of the quaternary salt.

The catalyst activity increased regularly with the number of carbon atoms in the alkyl group. Thus a less active system was obtained using tetramethyl ammonium bromide than when using tetrapropyl ammonium bromide. If one methyl group only was replaced with a longer chain (Test 2), the negative effect of the methyl group continued to influence the catalyst. If two methyl groups were replaced by larger groups, (Test 8), the positive effect of the long chains prevailed.

Replacement of all the methyl groups by phenyl groups (Test 10) produced a virtually inactive system, possibly due to encumbrance.

The nature of the halogen in the quaternary salt appears to be more important as regards catalyst activity. Chlorine based quaternary salts are more active (Tests 8 and 9); then bromine, then fluorine; iodine is practically inactive.

EXAMPLE 2

In this example, two catalytic systems, one based on [RhCl$_3$Br][NBu$_4$] and the other based on [RhCl$_3$Br][PBu$_4$] were used, each formed from a stoichiometric 1:1 mixture of the quaternary salt and rhodium trichloride.

It was demonstrated that the phosphonium salt had slight superiority as regards conversion, and otherwise the two systems were equivalent. Despite a 4 hour reaction time, formation of the 2:1 product was minimal in each case because of the use of the bromide.

TABLE 2

COMPARISON OF PHOSPHONIUM SALT AND AMMONIUM SALT

| Quaternary salt | $C_{18:2}$ ct weight % | $C_{18:2}$ tt weight % | Prd 1:1 weight % | Prd 2:1 weight % |
|-----------------|------------------------|------------------------|------------------|------------------|
| NBu$_4$Br       | 3.4                    | 15                     | 78.6             | 2.8              |
| PBu$_4$Br       | 2                      | 8.5                    | 85.5             | 4.1              |

REACTION CONDITIONS

RhCl$_3$, 3H$_2$O: 0.74 mmol,

Quaternary salt: 0.74 mmol,

Temperature: 90°–100° C.,

Pressure: 2 Mpa,

Duration: 4 hours.

EXAMPLE 3

In this example, a system constituted by rhodium chloride and a tetrabutyl ammonium bromide in a stoichiometry of 1:2 (1 rhodium to 2 quaternary salt) was used.

Better selectivity to that of Example 2 was obtained. The bromide based quaternary salts can thus be used for selective synthesis of the 1:1 addition product. It could further be seen that the solution was particularly homogeneous after the reaction.

TABLE 3

| Sample No | Time Minutes | Prd 1:1 weight % | Prd 2:1 weight % |
|-----------|--------------|------------------|------------------|
| 1         | 30           | 35               | 0                |
| 2         | 60           | 56               | 0                |
| 3         | 135          | 79               | 0                |

RhCl$_3$, 3H$_2$ O: 0.37 mmol

NBu$_4$Br: 0.74 mmol

CHCl$_3$: 25 ml

Conjugated $C_{18:2}$: 176 mmol

Temperature: 120° C.

Pressure: 3 MPa

The addition reaction was first order with respect to the starting substrate.

EXAMPLE 4

The Rh/P ratio was systematically changed in this example. With a Rh/P ratio of ¼, catalyst deactivation was observed. This latter system was, however, remarkably Selective for the 1:1 addition product. However, dimer formation was favoured in the long duration reactions (4–5 hours). Catalyst deactivation increased with the increasing quantity of phosphonium salt with respect to rhodium. A practically inactive system was thus obtained when the Rh/P ratio was ¹⁄₁₀. The phosphonium salt was tetraphenyl phosphonium bromide.

The results are shown in the following table:

TABLE 4

| No | Rh/P | Duration min | $C_{1:2}$ ct weight % | $c_{18:2}$ tt weight % | Prd 1:1 weight % |
|---|---|---|---|---|---|
| 1 | 1/4 | 156 | 10 | 20 | 70 |
|   |     | 227 | 7  | 16 | 71* |
|   |     | 427 | 1  | 12.8 | 76* |
| 2 | 1/6 | 120 | 55 | 28 | 17 |
| 3 | 1/10 | 60 | 77 | 14.5 | 8.5 |
|   |     | 130 | 73 | 17 | 10 | ct = cis trans
tt = trans trans
*Presence of dimers $RhCl_3, 3H_2O$: 0.23 mmol (Test 1), 0.38 mmol (Tests 2 and 3), Conjugated $C_{18:2}$: 173 mmol 109 mmol (Test 2) and 164 mmol (Test 3)

Temperature: 100°–120° C.,

Pressure: 3 MPa.

EXAMPLE 5

This example showed the possibility of operating with a very small quantity of catalyst.

The molar ratio of methyl ester of conjugated sunflower seed oil/rhodium was 19.17 and the ester/Rh weight ratio was 5500.

TABLE 5

CODIMERIZATION OF THE METHYL ESTER OF
CONJUGATED SUNFLOWER SEED OIL AND
ETHYLENE AT LOW CATALYST CONCENTRATIONS

| No | Duration min | $C_{18:2}$ ct weight % | $C_{18:2}$ tt weight % | Prd 1:1 weight % |
|---|---|---|---|---|
| 1 | 54 | 22 | 39.6 | 38 |
| 2 | 130 | 13.5 | 23 | 63 |
| 3 | 190 | 7.2 | 17 | 77 |

$RhCl_3, 3H_2O$: 0.14 mmol, $PBu_4Cl$: 0.14 mmol,

Temperature: 100° C.,

Pressure: 3 Mpa,

Ester: 268 mmol.

Here again, it can be seen that almost as much time was required for 50% conversion as that required for 50–75% conversion, indicating a first order reaction. The catalyst was not destroyed. The half reaction time was of the order of 90 min.

EXAMPLE 6

The flexibility of the catalytic system of the invention was demonstrated in this example, showing particular activity even at low pressures.

The following reactants were employed: 0.74 mmol of $RhCl_3, 3H_2O$; 0.74 mmol of $PBu_4Cl$; 25 ml of $CHCl_3$; 290 mmol of conjugated $C_{18:2}$.

The pressure was 0.3 to 0.4 MPa and the temperature was 96° C.

The product obtained was primarily the 1:1 product. After 3 hours of reaction, 29% of the 1:1 reaction product had been produced.

EXAMPLE 7

The catalyst was synthesized as described in the preceding examples, except that THF was used instead of $CHCl_3$.

TABLE 6

INFLUENCE OF THF

| No | Duration min | $C_{18:2}$ ct weight % | $C_{18:2}$ tt weight % | Prd 1:1 weight % |
|---|---|---|---|---|
| 1 | 20 | 64 | 22.8 | 13 |
| 2 | 39 | 38 | 27.6 | 30.4 |
| 3 | 80 | 24.5 | 32 | 43 |
| 4 | 146 | 19 | 29.5 | 51.5 |
| 5 | 186 | 16 | 28 | 55.6 |

$RhCl_3, 3H_2O$: 0.37 mmol, $PBu_4Cl$: 0.37 mmol,

THF: 15 ml,

Conjugated $C_{18:2}$: 91 mmol,

Temperature: 95°–110° C.,

Pressure: 2 Mpa.

THF was not as good a solvent as chloroform. Nevertheless, the $[RhCl_4][PBu_4]$ system in THF performed better than the $RhCl_3,3H_2O$ alone in chloroform. It can be seen here that the system was not first order. The catalyst deactivated progressively.

EXAMPLE 8

This example demonstrated the difference in reactivity between rhodium chloride and a quaternary salt. The rhodium chloride reactivity was so low that it was necessary to use more rhodium than normal to establish any comparison.

Test no 8.1: Quaternary salt system.

TABLE 7

| No | Duration min | $C_{18:2}$ ct weight % | $C_{18:2}$ tt weight % | Prd 1:1 weight % | Prd 2:1 weight % |
|---|---|---|---|---|---|
| 1 | 49 | 8.4 | 16 | 70 | 3.9 |
| 2 | 104 | 0 | 0 | 66.8 | 31.4 |
| 3 | 184 | 0 | 0 | 51 | 49 |
| 4 | 284 | 0 | 0 | 45 | 55 |

$RhCl_3, 3H_2O$: 1.48 mmol, $PBu_4Cl$: 1.48 mmol, $CHCl_3$: 25 ml,

Heptane: 100 ml,

Conjugated $C_{18:2}$: 91 mmol,

Temperature: 95°–100° C.,

Pressure: 2 Mpa.

It can be seen that there was quite substantial isomerizing activity in heptane since only 8,4% of the cis-trans compound remained after 50 minutes of reaction.

Test no 8.2: Test without quaternary salt.

TABLE 8

| No | Duration min | $C_{18:2}$ ct weight % | $C_{18:2}$ tt weight % | Prd 1:1 weight % | Prd 2:1 weight % |
|---|---|---|---|---|---|
| 1 | 50 | 68 | 23.5 | 8.5 | 0 |
| 2 | 164 | 32 | 40 | 26 | 0 |
| 3 | 249 | 21.3 | 37.2 | 38 | 1.6 |

TABLE 8-continued

| No | Duration min | C$_{18:2}$ ct weight % | C$_{18:2}$ tt weight % | Prd 1:1 weight % | Prd 2:1 weight % |
|---|---|---|---|---|---|
| 4 | 364 | 13 | 31 | 54 | 2 |
| 5 | 639 | 9 | 17 | 69 | 5 |
| 6 | 844 | 3.7 | 13.4 | 71 | 13 |
| 7 | 1200 | 0 | 8 | 73 | 19 |

The reaction conditions used were the same as those for Test no 8.1.

104 minutes were required to remove the dienes using the quaternary salt system and more than 1200 minutes using the rhodium chloride system; if it is assumed that the reaction was first order with respect to the substrate, the reaction summarized in Table 7 was in fact 15 times faster and completely removed the diene.

EXAMPLE 9

This example demonstrated that some phosphoranes produce similar results to those of the quaternary phosphonium salt.

TABLE 9

PHOSPHORANE SYSTEM

| No | Duration min | C$_{18:2}$ ct weight % | C$_{18:2}$ tt weight % | Prd 1:1 weight % | Prd 2:1 weight % |
|---|---|---|---|---|---|
| 1 | 96 | 0 | 2 | 89 | 9 |
| 1 | 181 | 0 | 0 | 83 | 17 |

RhCl$_3$, 3H$_2$O: 0.37 mmol,
Phosphorane: 0.37 mmol,
Chloroform: 20 ml,
Conjugated C$_{18:2}$: 171 mmol,
Temperature: 140° C.,
Pressure: 2.5 Mpa.
The formula for the phosphorane is

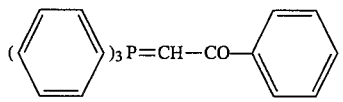

96 minutes were needed to obtain 98% of converted product, corresponding to 310 moles of product formed/hour/mole of rhodium assuming a first order reaction for the catalyst, which was not precisely the case. According to the previous example 1200 minutes were required to obtain complete conversion when using rhodium chloride, equivalent to 3 moles of product formed/mole of rhodium/hour. The activity ratio was of the order of 100.

EXAMPLE 10

A supported catalyst was used in this example.

0.1 g (0.37 mmol) of RhCl$_3$,3H$_2$O was stirred in a flask with 1 g (0.85 mmol) of tributylpolystyryl ammonium chloride (sold by FLUCKA) in 20 ml of chloroform. This was allowed to react for 5 hours. The resin fixing the rhodium was filtered and washed with chloroform then dried. The filtrate was colourless.

149 mmol of the methyl ester of 52% conjugated sunflower seed oil and 60 ml of n-heptane were employed. Ethylene was introduced to a pressure of 2 MPa and heated to a temperature of 110° C. The quaternary salt/Rh ratio was 2.29.

TABLE 10

| No | Duration min | C$_{18:2}$ tc weight % | C$_{18:2}$ tt weight % | Prd 1:1 weight % |
|---|---|---|---|---|
| 1 | 30 | 59 | 21.3 | 19 |
| 2 | 191 | 24 | 25.8 | 33 |
| 3 | 371 | 11.5 | 20.7 | 64.4 |

This test showed considerable slowing after 30 minutes of reaction. The rate decreased by a factor of 3.

EXAMPLE 11

A catalytic solution was synthesised from 0.74 mmol of trihydrated rhodium trichloride and 1.48 mmol of tetrabutyl phosphonium chloride in 10 ml of water. 299 mmol of the methyl ester of 52% conjugated sunflower seed oil was mixed with 2 MPa of ethylene at a temperature of 80° C. This was left to react for 195 minutes and 3.4,% by weight of the 1:1 addition product was obtained. The two-phase aqueous system did not appear to be very active in this case.

EXAMPLE 12

This example demonstrated that the catalyst was particularly active even with unconjugated esters, in this case methyl linoleate.

TABLE 12

REACTION OF METHYL ESTER OF SUNFLOWER SEED OIL WITH ETHYLENE

| No | Duration min | C$_{18:2}$ weight % | C$_{18:2}$ ct weight % | C$_{18:2}$ tt weight % | Prd 1:1 weight % |
|---|---|---|---|---|---|
| 1 | 0 | 100 | 0 | 0 | 0 |
| 2 | 14 | 65 | 10 | 13 | 12 |
| 3 | 43 | 59.5 | 7.5 | 12 | 21 |
| 4 | 103 | 54.8 | 4.4 | 9.6 | 33.4 |
| 5 | 163 | 44.5 | 3 | 7.5 | 44.9 |
| 6 | 278 | 38.7 | 1.5 | 6.8 | 50.1 |

RhCl$_3$, 3H$_2$O: 0.44 mmol,
PBu$_4$Cl: 0.44 mmol,
C$_{18:2}$: 161.5 mmol,
Temperature: 100° C.,
Pressure: 3 Mpa.

The figures given in Table 12 correspond to the diene present in the sunflower seed methyl ester.

It is clear from Table 12 that the linoleic ester was initially cis/trans conjugated and then the trans/trans isomer before addition of ethylene. Conjugation was predominant during the first part of the reaction. At the end of the reaction, a color change was observed in the reaction solution. It changed from red to black, whereas with a conjugated ester it remained red. The conjugation step could be the slow step in the reaction and the catalyst gradually deactivates during the reaction as if the initial presence of the conjugated diene stabilizes the reaction.

EXAMPLE 13

This example demonstrated the reactivity of the catalytic system with simple conjugated dienes. Piperylene was reacted with ethylene.

The catalytic solution was constituted by 0.74 mmol of trihydrated rhodium trichloride, 0.74 mmol of tetrabutyl phosphonium chloride and 30 ml of chloroform. 501 mmol of piperylene was mixed with 2 MPa of ethylene. This was allowed to react for 60 minutes at 80° C. to obtain 96% of 3-methyl 1,4-hexadiene, 3% of piperylene and traces of a heavier product.

The product was separated from the catalyst by distillation in argon. The remainder was then reused as the catalytic solution in a new addition reaction. 501 mmol of piperylene was reacted with ethylene for 215 minutes under the conditions given for the preceding reaction. 42% of 3-methyl 1,4-hexadiene was obtained, a 42% conversion rate.

EXAMPLE 14

In this example, 299 mmol of a 57% conjugated sunflower seed acid was reacted with ethylene in the presence of a catalytic solution composed of 1.1 mmol of rhodium trichloride and. 1.1 mmol of tetrabutyl phosphonium chloride in 25 ml of chloroform. The reaction was carried out at 90° C. at a pressure of 2 MPa of ethylene. After 7 hours 30 minutes of reaction, the following mixture was obtained after hydrogenation:

72% by weight of the 1:1 product, 19% by weight of the 2:1 product (diethyl) and 5% by weight of the 2:1 product (isobutyl).

We claim:

1. A process for the production of a co-dimer, comprising adding at least one monoolefin to a compound containing at least two conjugated or unconjugated ethylene bonds, in the presence of a catalytic system comprising a rhodium compound and a quaternary salt corresponding to the general formula

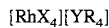
[RhX$_4$][YR$_4$]

where X represents a halogen ion or a SO$_4^{--}$, SO$_3^-$, OH$^-$, OR$^-$ or R$^-$ group, at least one X being a halide, Y represents a nitrogen atom or a phosphorous atom and R represents an alkyl, cycloalkyl, alkenyl, aryl, alkylaryl, polystyryl, alkyl polystyryl or acyl radical.

2. A process according to claim 1, wherein said monoolefin is selected from the group consisting of monoolefinic hydrocarbons, halogenated monoolefins, monoolefins containing carboxylic groups and moolefins containing nitrile groups.

3. A process according to claim 2, wherein said monoolefin is ethylene, propylene, 1-butene, vinyl chloride, methyl acrylate, acrylonitrile, allyl acetate vinyl acetate.

4. A process according to claim 1, wherein said compound comprising at least two ethylene bonds is a conjugated or conjugatable, aliphatic or cyclic diene or a diene, triene or tetraene compound containing a carboxylic function wherein the ethylene bonds are conjugated or conjugatable.

5. A process according to claim 4, wherein said compound containing at least two ethylene bonds is 1,3-butadiene, piperylene or isoprene.

6. A process according to claim 4, wherein said compound containing at least two ethylene bonds is a monocarboxylic acid containing 14 to 26 carbon atoms or esters thereof formed with a mono-, di- or trifunctional aliphatic alcohol containing 1 to 18 carbon atoms.

7. A process according to claim 6, wherein alcohol is methanol, ethanol, neopentylglycol, trimethylolpropane or glycerol.

8. A process according to claim 6, wherein said monocarboxylic acid or ester thereof is derived from natural plant or vegetable oils.

9. A process according to claim 1, wherein the rhodium compound in the catalytic system comprises a hydrated rhodium chloride and the quaternary salt comprises a compound of type NR$_4$X or PR$_4$X, where R is a methyl, ethyl, propyl, butyl, pentyl, hexyl, octyl, decyl, dodecyl, hexadecyl, octadecyl, benzyl, polystyryl or methylpolystyryl radical.

10. A process according to claim 1, wherein the reaction is carried out using at least one solvent at a pressure of 0.1 to 30 MPa and a temperature of 20° C. to 160° C.

11. A process according to claim 3, wherein said compound comprising at least two ethylene bonds is a conjugated or conjugatable, aliphatic or cyclic diene; or a diene, triene or tetraene compound containing a carboxylic function wherein the ethylene bonds are conjugated or conjugatable.

12. A process according to claim 11, wherein said compound containing at least two ethylene bonds is 1,3-butadiene, piperylene or isoprene.

13. A process according to claim 11, wherein said compound containing at least two ethylene bonds is a monocarboxylic acid containing 14 to 26 carbon atoms or esters thereof formed with a mono-, di- or trifunctional aliphatic alcohol containing 1 to 18 carbon atoms.

14. A process according to claim 13, wherein said alcohol is methanol, ethanol, neopentylglycol, trimethylopropane or glycerol.

15. A process according to claim 12, wherein the rhodium compound in the catalytic system comprises a hydrated rhodium chloride and the quaternary salt comprises a compound of the formula NR$_4$X or PR$_4$X, where R is a methyl, ethyl, propyl, butyl, pentyl, hexyl, octyl, decyl, dodecyl, hexadecyl, octadecyl, benzyl, polystyryl or methylpolystyryl radical.

16. A process according to claim 13, wherein the rhodium compound in the catalytic system comprises a hydrated rhodium chloride and the quaternary salt comprises a compound of the formula NR$_4$X or PR$_4$X, where R is a methyl, ethyl, propyl, butyl, pentyl, hexyl, octyl, decyl, dodecyl, hexadecyl, octadecyl, benzyl, polystyryl or methylpolystyryl radical.

17. A process according to claim 9, wherein the quaternary salt comprises a compound of the formula NR$_4$X.

18. A process according to claim 9, wherein the quaternary salt comprises a compound of the formula PR$_4$X.

* * * * *